US008306960B2

(12) United States Patent  
Kakimoto et al.

(10) Patent No.: US 8,306,960 B2  
(45) Date of Patent: Nov. 6, 2012

(54) MEDICAL IMAGE RETRIEVAL SYSTEM

(75) Inventors: Mitsuru Kakimoto, Kawasaki (JP); Takeichiro Nishikawa, Yokohama (JP); Hideyuki Aisu, Kawasaki (JP); Kenichi Niwa, Otawara (JP); Masakazu Osada, Otawara (JP); Takashi Masuzawa, Otawara (JP); Shinichiro Hamada, Kawasaki (JP)

(73) Assignees: Kabushiki Kaisha Toshiba, Tokyo (JP); Toshiba Medical Systems Corporation, Tochigi (JP)

( * ) Notice: Subject to any disclaimer, the term of this patent is extended or adjusted under 35 U.S.C. 154(b) by 427 days.

(21) Appl. No.: 12/038,590

(22) Filed: Feb. 27, 2008

(65) Prior Publication Data

US 2008/0215525 A1 Sep. 4, 2008

(30) Foreign Application Priority Data

Feb. 28, 2007 (JP) .................................. 2007-050784

(51) Int. Cl.
 *G06F 7/00* (2006.01)
 *G06F 17/30* (2006.01)

(52) U.S. Cl. ........................................................ 707/705

(58) Field of Classification Search .................. 707/705, 707/999.1
 See application file for complete search history.

(56) References Cited

U.S. PATENT DOCUMENTS

| 5,452,416 | A  | * | 9/1995  | Hilton et al. ................... 715/783 |
| 5,779,634 | A  | * | 7/1998  | Ema et al. ...................... 600/407 |
| 5,807,256 | A  | * | 9/1998  | Taguchi et al. ................. 600/425 |
| 5,839,438 | A  | * | 11/1998 | Graettinger et al. ........... 600/300 |
| 6,006,191 | A  | * | 12/1999 | DiRienzo ........................... 705/2 |
| 6,292,577 | B1 | * | 9/2001  | Takahashi ....................... 382/128 |
| 6,697,506 | B1 | * | 2/2004  | Qian et al. ....................... 382/128 |
| 7,054,473 | B1 | * | 5/2006  | Roehrig et al. ................. 382/128 |
| 7,184,582 | B2 | * | 2/2007  | Giger et al. ..................... 382/128 |
| 7,244,230 | B2 | * | 7/2007  | Duggirala et al. .............. 600/300 |
| 7,298,881 | B2 | * | 11/2007 | Giger et al. ..................... 382/128 |
| 7,458,936 | B2 | * | 12/2008 | Zhou et al. ...................... 600/437 |
| 2001/0043729 | A1 | * | 11/2001 | Giger et al. ..................... 382/128 |
| 2002/0016718 | A1 | * | 2/2002  | Rothschild et al. ............... 705/2 |
| 2002/0097902 | A1 | * | 7/2002  | Roehrig et al. ................. 382/132 |
| 2003/0013951 | A1 | * | 1/2003  | Stefanescu et al. ............ 600/407 |
| 2003/0103663 | A1 | * | 6/2003  | Li et al. ......................... 382/131 |

(Continued)

FOREIGN PATENT DOCUMENTS

JP 05-101122 4/1993

(Continued)

OTHER PUBLICATIONS

Swett, Henry A., et al., "Expert System-Controlled Image Display", Radiology, vol. 172, No. 2, Aug. 1989, pp. 487-493.*

(Continued)

*Primary Examiner* — Aleksandr Kerzhner  
(74) *Attorney, Agent, or Firm* — Turocy & Watson, LLP

(57) ABSTRACT

A medical image retrieval system includes an image database which stores medical images. An interpretation unit acquires a currently diagnosed image for use in performing interpretation of one of the medical images and provides the currently diagnosed image to a computer terminal. An image requesting unit issues an image request associated with the currently diagnosed image. An image retrieval unit retrieves a reference image from the image database in accordance with the image request and provides the reference image to the computer terminal in order to propose the reference image as references for diagnosis. An evaluation input unit prompts to input an evaluation indicating whether the reference image has been helpful for diagnosis based on the currently diagnosed image.

2 Claims, 10 Drawing Sheets

U.S. PATENT DOCUMENTS

| | | | |
|---|---|---|---|
| 2003/0233250 A1* | 12/2003 | Joffe et al. | 705/2 |
| 2004/0141639 A1* | 7/2004 | Matsui | 382/132 |
| 2004/0172292 A1* | 9/2004 | Takekoshi et al. | 705/2 |
| 2004/0184646 A1* | 9/2004 | Oosawa | 382/128 |
| 2004/0193036 A1* | 9/2004 | Zhou et al. | 600/407 |
| 2004/0247166 A1* | 12/2004 | Giger et al. | 382/128 |
| 2005/0020903 A1* | 1/2005 | Krishnan et al. | 600/407 |
| 2005/0041844 A1* | 2/2005 | Yamanaka | 382/128 |
| 2005/0152592 A1* | 7/2005 | Kasai | 382/132 |
| 2005/0251013 A1* | 11/2005 | Krishnan et al. | 600/407 |
| 2005/0288568 A1* | 12/2005 | Pan | 600/407 |
| 2006/0004278 A1* | 1/2006 | Giger et al. | 600/408 |
| 2006/0059145 A1* | 3/2006 | Henschke et al. | 707/6 |
| 2006/0064321 A1 | 3/2006 | Sasano et al. | |
| 2006/0274928 A1* | 12/2006 | Collins et al. | 382/132 |
| 2006/0277073 A1* | 12/2006 | Heilbrunn et al. | 705/3 |
| 2007/0003119 A1* | 1/2007 | Roehrig et al. | 382/128 |
| 2007/0081699 A1* | 4/2007 | Avinash et al. | 382/128 |
| 2007/0081700 A1* | 4/2007 | Blumenfeld et al. | 382/128 |
| 2007/0081701 A1* | 4/2007 | Sirohey et al. | 382/128 |
| 2007/0116336 A1* | 5/2007 | Mahesh et al. | 382/128 |
| 2007/0122018 A1* | 5/2007 | Zhou et al. | 382/128 |
| 2007/0127793 A1* | 6/2007 | Beckett et al. | 382/128 |
| 2007/0165924 A1* | 7/2007 | Nicponski | 382/128 |
| 2008/0118138 A1* | 5/2008 | Zingaretti et al. | 382/132 |
| 2008/0140708 A1* | 6/2008 | Fuerst et al. | 707/104.1 |
| 2009/0226065 A1* | 9/2009 | Chen | 382/131 |

FOREIGN PATENT DOCUMENTS

| | | |
|---|---|---|
| JP | 2002-230518 | 8/2002 |
| JP | 2003-126045 | 5/2003 |
| JP | 2003-162531 | 6/2003 |
| JP | 2003-316932 | 11/2003 |
| JP | 2005-085200 | 3/2005 |
| JP | 2006-034337 | 2/2006 |
| JP | 2006-061278 | 3/2006 |
| JP | 2006-155002 | 6/2006 |
| JP | 2006-271541 | 10/2006 |

OTHER PUBLICATIONS

Müller, Henning, et al., "A Reference Data set for the Evaluation of Medical Image Retrieval Systems", Computerized Medical Imaging and Graphics, vol. 28, Issue 6, Sep. 2004, pp. 295-305.*

Lowe, Henry J., et al., "Towards Knowledge-Based Retrieval of Medical Images. The Role of Semantic Indexing, Image Content Representation and Knowledge-Based Retrieval", Proc. AMIA Symp., © 1998, pp. 882-886.*

Armato III, Samuel G., et al., "Lung Image Database Consortium: Developing a Resource for the Medical Imaging Research Community", Radiology, vol. 232, No. 3, Sep. 2004, pp. 739-748.*

Seka, L. P., et al., "Computer Assisted Medical Diagnosis Using the Web", International Journal of Medical Informatics, vol. 47, Issues 1-2, Nov. 1997, pp. 51-56.*

Macura, Katarzyna J., et al., "Digital Case Library: A Resource for Teaching, Learning and Diagnosis Support in Radiology", RadioGraphics, Jan. 1995, pp. 156-164.*

Lim, C. C. Tchoyoson, et al., "Medical Image Resource Center-Making Electronic Teaching Files from PACS", Journal of Digital Imaging, vol. 16, No. 4, Dec. 2003, pp. 331-336.*

Swett, Henry A., et al., "The Image/Icon System: Voice Activated Intelligent Image Display for Radiologic Diagnosis", American Medical Informatics Association (AMIA), Proc. of the Annual Symposium on Computer Application in Medical Care, Nov. 1989, pp. 977-978.*

Petrakis, E. G. M., et al., "Similarity Searching in Medical Image Databases", IEEE Transactions on Knowledge and Data Engineering, vol. 9, No. 3, May/Jun. 1997, pp. 435-447.*

The American Heritage College Dictionary, 4th Edition, Houghton Mifflin Co., Boston, MA, © 2002, pp. 73 and 77.*

Wong, Stephen T. C., et al., "Design Methods and Architectural Issues of Integrated Medical Image Data Base Systems", Computerized Medical Imaging and Graphics, vol. 20, Issue 4, Jul.-Aug. 1996, pp. 285-299.*

Tombropoulos, Rhea, et al., "A Decision Aid for Diagnosis of Liver Lesions on MRI", AMIA Proc. Annu. Symp. Comput. Appl. Med. Care, Washington, DC, Oct. 30-Nov. 3, 1993, pp. 439-443.*

Traina, Agma, et al., "Integrating Images to Patient Electronic Medical Records through Content-based Retrieval Techniques", CBMS '03, © 2003, 6 pages.*

Tleyjeh, Imad M., et al., "VisualDx: Decision-Support Software for the Diagnosis and Management of Dermatologic Disorders", Clinical Infectious Diseases, vol. 43, No. 9, Nov. 1, 2006, pp. 1177-1184.*

Macura, Katarzyna J., et al., "Digital Case Library: A Resource for Teaching, Learning, Diagnosis Support in Radiology", RadioGraphics, vol. 15, No. 1, Jan. 1995, pp. 155-164.*

Japanese Office Action for Japanese Application No. 2007-050784 mailed on Oct. 18, 2011.

Japanese Office Action for Japanese Application No. 2007-050784 mailed on May 8, 2012.

* cited by examiner

| Patient name | Hikatyu | Hikozaru | Bochama | Nae |
|---|---|---|---|---|
| Initially predicted disease name | Gastric ulcer | No problem | Gastric cancer | Gallbladder polyp |
| Disease candidate | Gastric cancer | — | — | — |
| Predicted disease name | Gastric ulcer | — | Gastric cancer | Gallbladder polyp |
| Confirmed disease name | Gastric cancer | Cerebral infarct | No problem | Gallbladder polyp |

F I G. 3

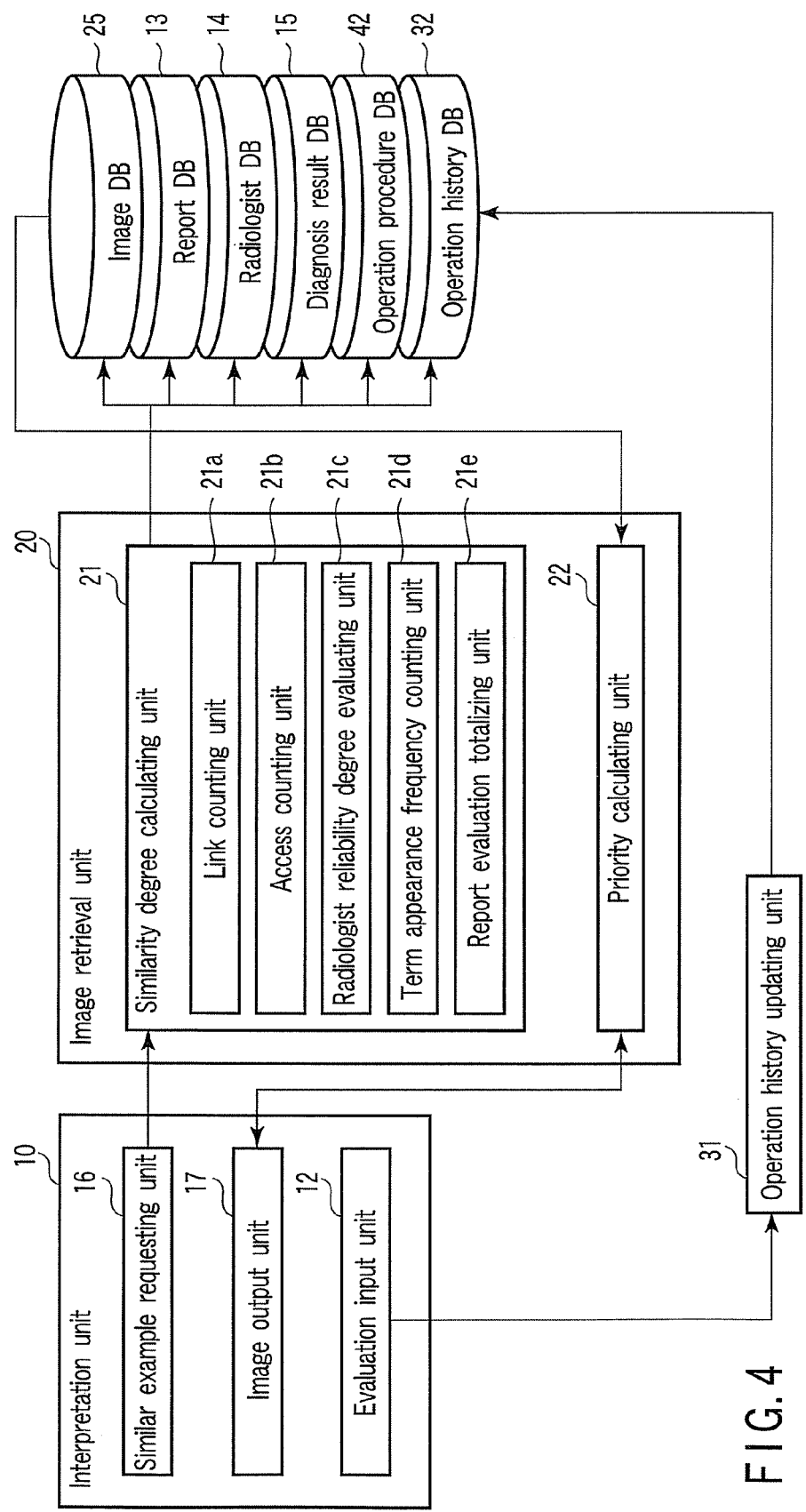
F I G. 4

FIG. 5

| Image | Numerical information | | | | Attribute information | | | |
|---|---|---|---|---|---|---|---|---|
| | Numerical information 1 | Numerical information 2 | ...... | Numerical information N | Number of links | Number of accesses | Radiologist reliability | Term appearance frequency |
| 000001 | | | | | | | | |
| 000002 | | | | | | | | |
| 000003 | | | | | | | | |

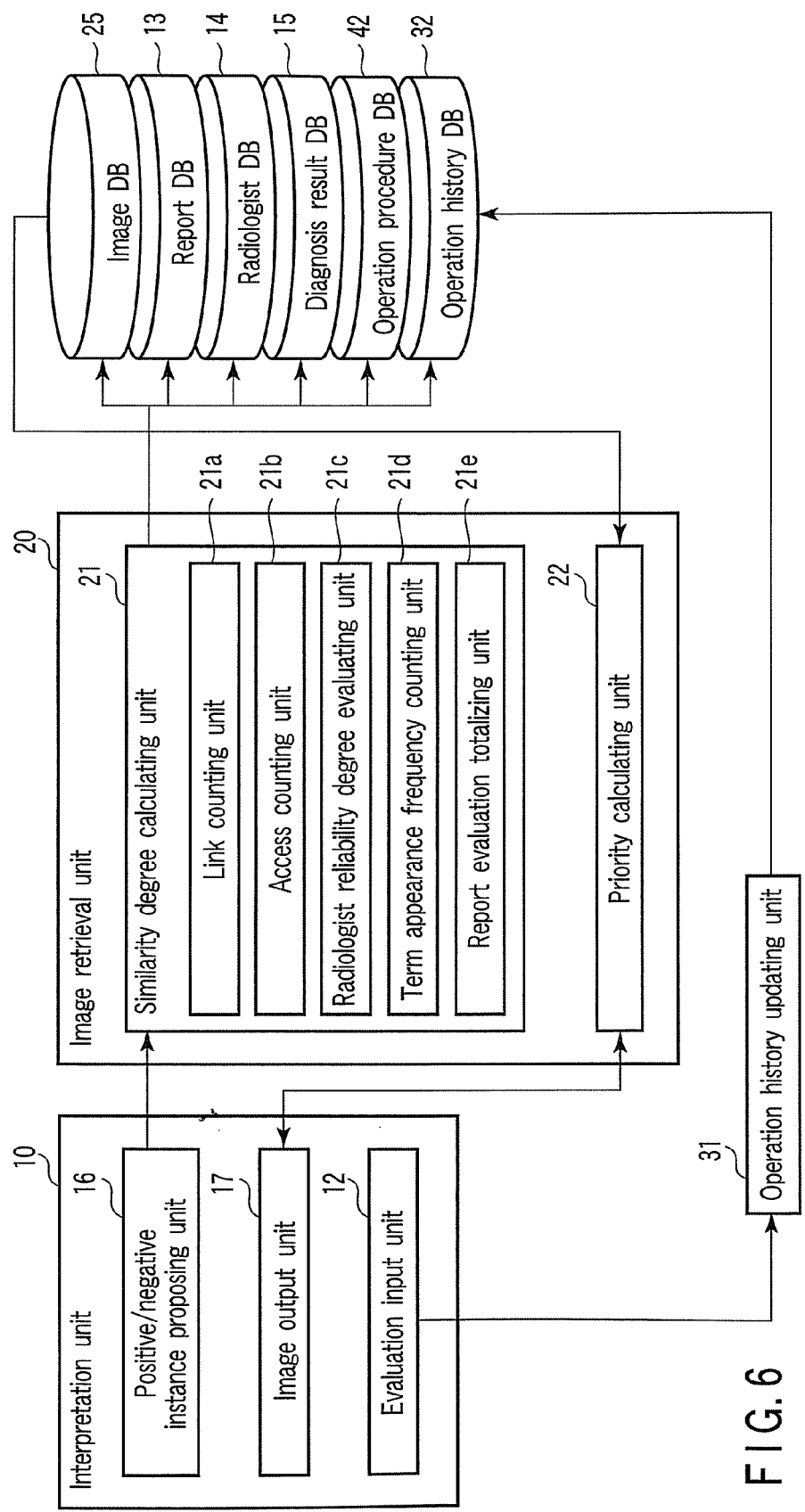
F I G. 6

| Predicted disease name/ confirmed disease name | A | B | C | D | No problem | Total |
|---|---|---|---|---|---|---|
| A | 91 | 3 | 1 | 0 | 7 | 102 |
| B | 0 | 189 | 1 | 2 | 1 | 193 |
| C | 1 | 2 | 33 | 1 | 0 | 37 |
| D | 1 | 2 | 5 | 113 | 3 | 124 |
| No problem | 0 | 2 | 1 | 5 | 222 | 230 |

FIG. 7

| Predicted disease name/ confirmed disease name | A | B | C | D | No problem |
|---|---|---|---|---|---|
| A | 89.2 | 2.9 | 1.0 | 0.0 | 6.9 |
| B | 0.0 | 97.9 | 0.5 | 1.0 | 0.5 |
| C | 2.7 | 5.4 | 89.2 | 2.7 | 0.0 |
| D | 0.8 | 1.6 | 4.0 | 91.1 | 2.4 |
| No problem | 0.0 | 0.9 | 0.4 | 2.2 | 96.5 |

FIG. 8

| Predicted disease name/ confirmed disease name | A | B | C | D | No problem |
|---|---|---|---|---|---|
| A | 0 | 6 | 4 | 3 | 3 |
| B | 7 | 0 | 5 | 2 | 2 |
| C | 8 | 4 | 0 | 2 | 2 |
| D | 9 | 5 | 1 | 0 | 1 |
| No problem | 10 | 8 | 6 | 5 | 0 |

FIG. 9

| Predicted disease name/ confirmed disease name | A | B | C | D | No problem |
|---|---|---|---|---|---|
| A | 0.0 | 17.6 | 3.9 | 0.0 | 20.6 |
| B | 0.0 | 0.0 | 2.6 | 2.1 | 1.0 |
| C | 21.6 | 21.6 | 0.0 | 5.4 | 0.0 |
| D | 7.3 | 8.1 | 4.0 | 0.0 | 2.4 |
| No problem | 0.0 | 7.0 | 2.6 | 10.9 | 0.0 |

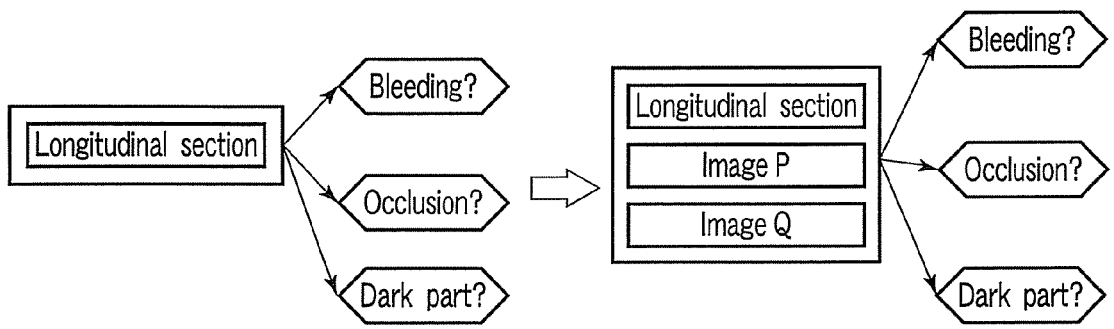
F I G. 14
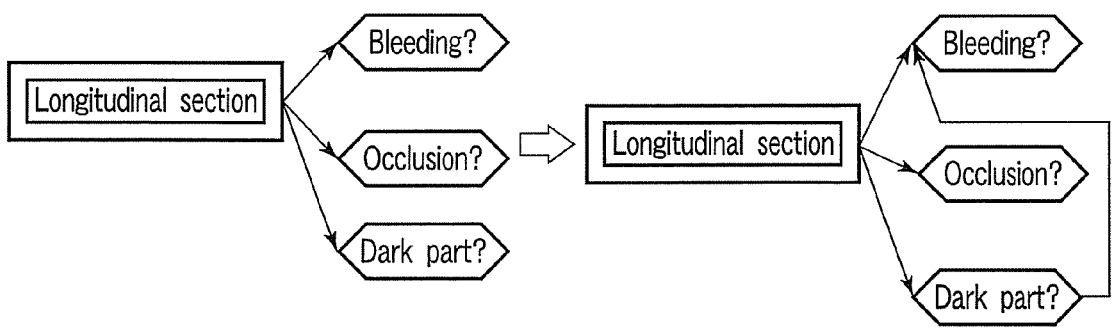
F I G. 15

MEDICAL IMAGE RETRIEVAL SYSTEM

CROSS-REFERENCE TO RELATED APPLICATIONS

This application is based upon and claims the benefit of priority from prior Japanese Patent Application No. 2007-050784, filed Feb. 28, 2007, the entire contents of which are incorporated herein by reference.

BACKGROUND OF THE INVENTION

1. Field of the Invention

The present invention relates to a system which retrieves a medical image serving as a reference for the interpretation of a medical image.

2. Description of the Related Art

A radiologist for medical images is required to determine from a large number of images whether, for example, there is a lesion or a given tumor is benign or malignant. Various techniques have therefore been proposed to support diagnosis. For example, there has been proposed an apparatus which can support diagnosis in accordance with the purpose or contents of diagnosis by allowing selective use of diagnosis support contents prepared in advance (see JP-A No. 2003-126045 (KOKAI). There has also been proposed a system which automatically outputs medical information concerning medical images by associating the feature amount of a region of interest with the medical information (see JP-A No. 2006-34337 (KOKAI)). A radiologist can efficiently perform image diagnosis while referring to the diagnosis result obtained by another radiologist. CAD (Computer-Aided Detection) systems which aid radiologists have been introduced into many medical institutions. The CAD systems derive numerical values characterizing medical images. Currently, however, there is no simple mechanism which automatically retrieves images as references for radiologists.

BRIEF SUMMARY OF THE INVENTION

According to an aspect of the present invention, there is provided a medical image retrieval system comprising an image database which stores medical images. An interpretation unit acquires a currently diagnosed image for use in performing interpretation of one of the medical images and provides the currently diagnosed image to a computer terminal. An image requesting unit issues an image request associated with the currently diagnosed image. An image retrieval unit retrieves a reference image from the image database in accordance with the image request and provides the reference image to the computer terminal in order to propose the reference image as references for diagnosis. An evaluation input unit prompts to input an evaluation indicating whether the reference image has been helpful for diagnosis based on the currently diagnosed image.

BRIEF DESCRIPTION OF THE SEVERAL VIEWS OF THE DRAWING

FIG. 3 is a view showing specific examples from initially predicted disease names to confirmed disease names;

FIG. 4 is a block diagram showing the schematic arrangement of the main part of a medical image retrieval system according to the second embodiment;

FIG. 5 is a view showing an example of a format for recording numerical value information extracted from a report and attribute information including the number of links, the number of accesses, a radiologist reliability degree, and a term appearance frequency;

FIG. 6 is a block diagram showing the main part of a medical image retrieval system according to the third embodiment;

FIG. 7 is a view showing an example of a table of examination names and predicted disease names and confirmed disease names for the respective examination regions;

FIG. 8 is a view showing the ratios of the numbers of cases with confirmed disease names to the total numbers of cases with predicted disease names;

FIG. 9 is a view showing an example of a loss table;

FIG. 14 is a view showing an example of an automatically corrected operation template; and FIG. 15 is a view showing another example of an automatically corrected operation template.

DETAILED DESCRIPTION OF THE INVENTION

The embodiments of the present invention will be described with reference to the views of the accompanying drawing.

First Embodiment

Figure 1:
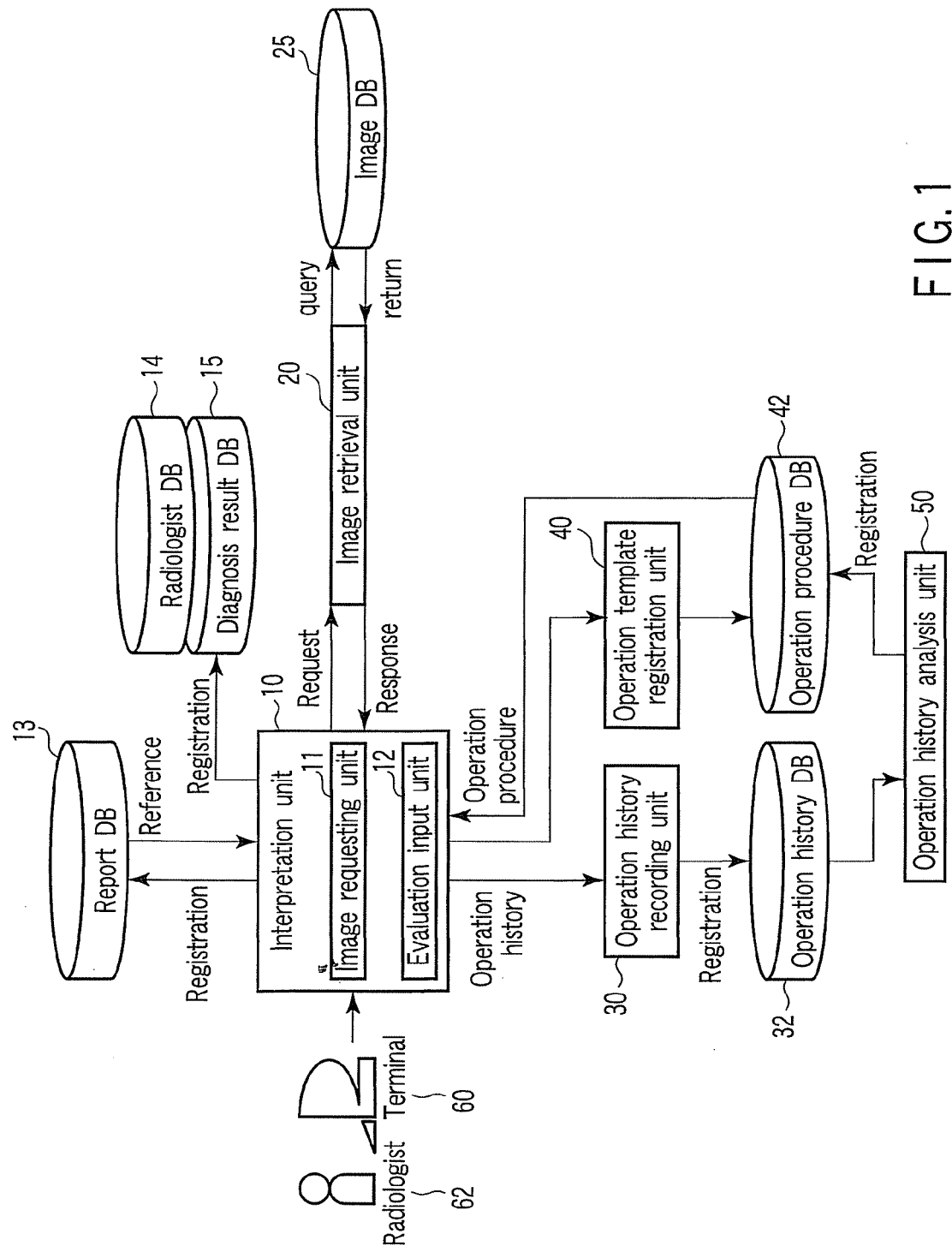
FIG. 1 is a block diagram showing a medical image retrieval system according to the first embodiment.

Referring to FIG. 1, a medical image retrieval system according to the first embodiment basically includes a dedicated computer system including a CPU, memory, and external storage device. A specific example of this arrangement will be omitted.

The medical image retrieval system according to the present embodiment includes an interpretation unit 10, image retrieval unit 20, operation history recording unit 30, operation template registration unit 40, and operation history analysis unit 50. The interpretation unit 10 further includes an image requesting unit 11 and an evaluation input unit 12. The above units are connected to various types of databases (each of which will be referred to as a "DB" in this specification) necessary for diagnosis and the like. This system includes an image DB 25, a report DB 13, diagnosis result DB 15, radiologist DB 14, operation history DB 32, and operation procedure DB 42 as databases according to this embodiment. These databases are connected to each other via links. The operation of the medical image retrieval system including this arrangement will be described.

A radiologist 62 performs diagnosis on an image captured in an examination by accessing the interpretation unit 10 via a computer terminal. As a result of this diagnosis, the radiologist 62 generates a report which is a text explaining the details of the diagnosis. This report is registered in the report DB 13 via the interpretation unit 10. In addition, the position of a lesion and its disease name are registered in the diagnosis result DB 15.

In this context, the radiologist 62 can refer to images other than the image captured in the examination, which he/she is currently examining, during diagnosis. In this embodiment, the interpretation unit 10 includes the image requesting unit 11 which proposes images as references for diagnosis. The radiologist can start the image requesting unit 11 by operation on the screen of the terminal 60. The image requesting unit 11 issues a request to the image retrieval unit 20 in accordance with what kind of image is requested. The image retrieval unit 20 extracts an image matching the request from the image DB 25 by using information in various types of DBs to be described in detail later, and returns the image as a response to the interpretation unit 10. The interpretation unit 10 includes the evaluation input unit 12. The radiologist 62 evaluates an image retrieved via the terminal 60 in terms of whether the image has been helpful or not, and inputs the corresponding information by using the evaluation input unit 12. For example, the radiologist grades an image on a scale of 100 and inputs the resultant numerical value, with "100" representing that the image has been very helpful, and "0" representing that the image has not been helpful at all. To simplify an evaluation input process, another embodiment is configured to grade a given recommended image as 100 when the radiologist has seen the image, and to grade the image as 0 when he/she has not seen it. Still another embodiment is configured to determine the usefulness of a given image depending on the time interval in which the radiologist has paid attention to the image. This embodiment measures the time during which a given image has been displayed, and grades the image as "100" if the time is equal to or more than a given threshold, and as "0" if the time is equal to or less than the threshold. The medical image retrieval system also includes the operation history recording unit 30 in which a history of operations performed by the radiologist 62 is stored. The operation history recording unit 30 outputs this input value to the operation history DB 32.

The radiologist 62 can refer to some kind of standard procedure when performing diagnosis. The radiologist 62 can embody such a procedure as an operation sequence when using the interpretation unit 10. The description of this operation sequence will be referred to as an "operation template" in this specification. The manner of using such an operation template will be simply described below.

First a diagnosis specialist describes a diagnosis method as an operation sequence for the interpretation unit 10 via the operation template registration unit 40 and registers it in the operation procedure DB 42, thereby generating an initial operation template. When referring to this operation procedure template or performing diagnosis in accordance with it, the radiologist 62 loads the operation procedure from the operation procedure DB 42 into the interpretation unit 10. As a result, the interpretation unit 10 imposes restrictions on the display and order of windows to prompt the radiologist 62 to refer to the operation procedure or perform operation in accordance with the procedure.

As described above, the diagnosing operation by the radiologist 62 is registered in the operation history DB 32. An operation procedure is also generated from this information. The operation history analysis unit 50 derives an effective operation sequence from the operation history registered in the operation history DB 32, and registers the sequence as an operation template in the operation procedure DB 42. The radiologist 62 can refer to this operation template as well when performing diagnosis. The details of update operation and the like of an operation template will be described later.

Figure 2:
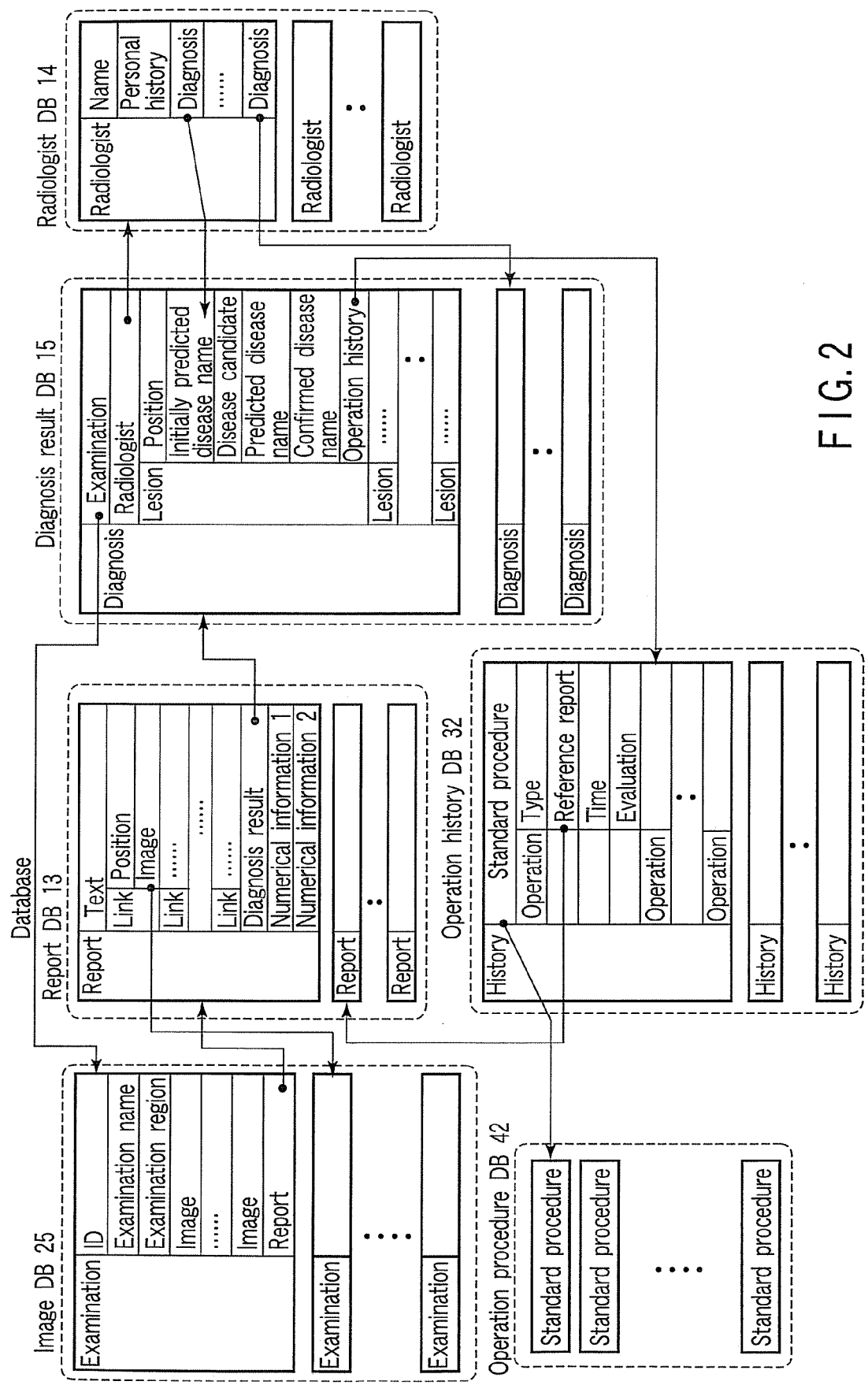
FIG. 2 is a view showing the details of the arrangement of each of databases and the relationship between links to them.

An example of the arrangement of each database will be described below with reference to FIG. 2. FIG. 2 shows the detailed arrangement of each of databases and the relationship between links to them. Note that this database arrangement is the same in each of the following embodiments. As shown in FIG. 2, the respective databases are not independent of each other, and links are set in the reference fields of associated databases.

<Image DB 25>

The image DB 25 is a database which stores sets of images captured for examinations in correspondence with each of the examinations. One examination entry has the following fields:
1) ID: the number for uniquely identifying an examination;
2) examination name: the type of image, e.g., a CT, MRI, or ultrasonic image;
3) examination region: an examined region of the body, e.g., the head, stomach, or lung;
4) image: an image or images captured in the examination; and
5) report: link information for the report generated by the radiologist 62 on the basis of the result of diagnosis on the examination identified by the examination ID, and link information for a report stored in the report DB 13.

<Report DB 13>

The report DB 13 is a database which stores the reports generated by the radiologist 62 to explain the details of diagnosis. A report is, for example, a hypertext document having link information for each referred image embedded in a text. One report entry has the following fields:
1) text: the text portion of the report;
2) link: a link to a reference image (including an image used for diagnosis) embedded in the report; having the following two subfields:
 a) position: the embedding position of link information in the text; and
 b) image: link information to the image DB 25 storing the embedded image
5) diagnosis result: link information to a diagnosis result entry in the diagnosis result DB 15 which corresponds to the report; and
6) numeral information: various kinds of numerical information about diagnosis, including, for example, vital numerical information (a body temperature, blood pressure, and the like), numerical information (the sizes of polyps and the number of polyps) obtained as a result of analysis using a CAD system, and a date.

<Diagnosis Result DB 15>

The diagnosis result DB 15 is a database storing summaries of diagnosis results obtained by the radiologist 62. A diagnosis result entry has the following fields:
1) examination: link information to an examination entry in the image DB 25 which designates an examination (or an examination ID) corresponding to a diagnosis result;
2) radiologist: link information to a radiologist entry in the radiologist DB 14 which designates the radiologist 62 who has performed diagnosis; and
3) lesion: a description about a lesion, which includes the following sub-fields:
 1) position: the position of the lesion in a human organ;
 2) initially predicted disease name: the disease name determined in initial diagnosis;
 3) disease candidate: a suspected disease name other than a diagnosed disease name (if any);
 4) predicted disease name: a predicted disease name (e.g., the disease name determined in a conference) at a given time point;

5) confirmed disease name: a disease name which has been determined when the patient is finally cured (released from the hospital) in the process of medical treatment for a patient; and 6) operation history: link information to an operation history entry in the operation history DB 32, which is an operation history of the radiologist 62 in diagnosis on this lesion.

FIG. 3 shows specific examples from initially predicted disease names to confirmed disease names. As shown in FIG. 3, when, for example, the initially predicted disease name based on image diagnosis on the patient "hikatyu" is gastric ulcer, another disease candidate may be gastric cancer. In this case, if "gastric cancer" is finally confirmed even though "gastric ulcer" is diagnosed in a conference, "gastric cancer" is recorded as a confirmed disease name. FIG. 3 also shows that although the patient "bochama" is initially diagnosed as having "gastric cancer", he is finally diagnosed having "no problem".

<Radiologist DB 14>

The radiologist DB 14 is a database which stores information about a radiologist who performs interpretation. A radiologist entry has the following fields:

1) name: the name of a radiologist;
2) personal history: the personal history of the radiologist; and
3) diagnosis: the history of all diagnoses performed by the radiologist 62 in the past, and link information to the diagnosis result entry in the diagnosis result DB 15.

<Operation History DB 32>

The operation history DB 32 is a database which stores the history of operation of the interpretation unit 10 by the radiologist 62. A history entry has the following fields:

1) standard procedure: an operation procedure which the radiologist 62 follows or to which he/she refers when performing interpretation, and link information to an entry in the operation procedure DB 42;
2) operation: operation performed by the radiologist 62 at the time of diagnosis, which includes the following subfields:
1) type: the type of operation performed by the radiologist with respect to the interpretation system at the time of diagnosis, which includes, for example, enlarging an image and measuring the size of a lesion;
2) reference report: a report to which the radiologist has referred when performing operation, and link information to an entry in the report DB 13;
3) time: the time when operation has been performed; and
4) evaluation: the degree to which a report has been referred, which is represented by, for example, a score.

<Operation Procedure DB 42>

The operation procedure DB 42 is a database which stores an operation procedure which the radiologist 62 follows or to which he/she refers when performing diagnosis. This operation procedure is registered as a standard operation procedure.

Second Embodiment

FIG. 4 is a block diagram showing the schematic arrangement of the main part of a medical image retrieval system according to the second embodiment. The second embodiment is configured to retrieve similar images in a concrete manner in the first embodiment. This embodiment includes an interpretation unit 10, similar example requesting unit 16, and image output unit 17. An image retrieval unit 20 includes a similarity degree calculating unit 21 and a priority calculating unit 22.

In the above arrangement, the similar example requesting unit 16 corresponds to the image requesting unit 11 in the first embodiment, and requests an image retrieval means to retrieve an image similar to a currently diagnosed image. The similar example requesting unit 16 is started by an instruction from a terminal 60 (not shown). The image output unit 17 outputs a retrieved image or link information to an image to the terminal 60.

The similarity degree calculating unit 21 includes a link counting unit 21a, access counting unit 21b, radiologist reliability degree evaluating unit 21c, term appearance frequency counting unit 21d, and report evaluation totalizing unit 21e. The similarity degree calculating unit 21 uses the value evaluated by each unit described above to perform calculation so as to determine which one of images which have been selected (to be referred to as "selected images" hereinafter) is similar to a currently diagnosed image (to be referred to as a "diagnosis image" hereinafter). The similarity degree calculating unit 21 extracts numerical information from a report.

The link counting unit 21a counts the number of hyperlinks to a selected image. As described above, when generating a report, a radiologist 62 embeds, in the report, images to which he/she has referred when performing determination. The number of hyperlinks is counted by counting the number of times "report: link: image" coincides with a selected image by scanning the report DB 13.

The access counting unit 21b counts the number of times all radiologists 62 using the medical image retrieval system have referred to a selected image in the past. More specifically, the access counting unit 21b extracts "diagnosis: lesion: operation history" by scanning a diagnosis result DB 15. The access counting unit 21b also extracts "history: operation: reference report" from a corresponding history in the operation history DB 32. The access counting unit 21b then extracts a corresponding entry of the report DB 13, and counts the number of times the value of "report: link: image" coincides with a selected image.

The radiologist reliability degree evaluating unit 21c evaluates the reliability degree of the radiologist 62 which has performed diagnosis on a selected image. The following is a specific evaluation method for the radiologist 62. First the radiologist reliability degree evaluating unit 21c extracts an examination including a selected image from an image DB 25, and extracts a report corresponding to the examination from "examination: report". The radiologist reliability degree evaluating unit 21c extracts "report: diagnosis result" from the corresponding report in the report DB 13. The radiologist reliability degree evaluating unit 21c further extracts "diagnosis: radiologist" from the corresponding diagnosis result in the diagnosis result DB 15. In this stage, the radiologist 62 corresponding to the selected image is known. Assume that the radiologist 62 is radiologist A. The access counting unit 21b tracks all the diagnoses performed by the radiologist 62 by checking "radiologist: diagnosis" from a radiologist DB 14. The radiologist reliability degree evaluating unit 21c extracts "diagnosis: examination" from the diagnosis result DB 15. The radiologist reliability degree evaluating unit 21c can extract all the images diagnosed by radiologist A by extracting "examination: image" from the image DB 25. The radiologist reliability degree evaluating unit 21c calculates the number of links to each extracted image by using the link counting unit 21a. The radiologist reliability degree evaluating unit 21c obtains the sum of the numbers of links to all the images diagnosed by radiologist A and sets the sum as the reliability degree of radiologist A.

The term appearance frequency counting unit 21d extracts an examination including a selected image from the image DB 25, and extracts a report from "examination: report". Subsequently, the term appearance frequency counting unit 21*d* extracts a text from a report DB 13 by tracking "report: text". The term appearance frequency counting unit 21*d* counts the appearance frequency of an important term from the text. For simplicity, assume that the term appearance frequency counting unit 21*d* selects one term and counts its appearance frequency.

The report evaluation totalizing unit 21*e* estimates whether the evaluation of a report based on diagnosis on a selected image is high or low. The report evaluation totalizing unit 21*e* extracts "examination: report" from the examination on the selected image in the image DB 25, and extracts a report corresponding to the selected image. The report evaluation totalizing unit 21*e* then scans an operation history DB 32. If "history: operation: reference report" coincides with the extracted report, the report evaluation totalizing unit 21*e* adds the value of "history: operation: evaluation". The report evaluation totalizing unit 21*e* sets the resultant total value as the evaluation of the report.

The priority calculating unit 22 calculates the priorities of all retrieved images and outputs the images to the interpretation unit 10 in the decreasing order of priorities. As a method of calculating priorities, a method of assigning higher priorities to images with higher similarity degrees is conceivable. Most simply, it suffices to use a similarity degree as a priority. The priority calculating unit 22 extracts images with priorities higher than a given designated value or a given designated number of images in the decreasing order of priorities. A processing procedure in the medical image retrieval system according to this embodiment having the above arrangement will be briefly described below.

The radiologist 62 starts the similar example requesting unit 16 via the terminal 60 when he/she wants to see effective similar images to a currently diagnosed image. Assume that at this time, the radiologist 62 inputs a predicted disease name without fail. The similar example requesting unit 16 outputs the diagnosis image and the corresponding predicted disease name to the image retrieval unit 20.

The image retrieval unit 20 scans the diagnosis result DB 15 to retrieve all diagnoses having a lesion matching the predicted disease name, and extracts images associated with examinations corresponding to the diagnoses from the image DB 25. The similar example requesting unit 16 then picks up images included in these examinations as candidates of images to be retrieved.

The similarity degree calculating unit 21 records in advance the numerical information extracted from the report and attribute information including the number of links, the number of accesses, a radiologist reliability degree, and a term appearance frequency in the format shown in FIG. 5. A similarity degree is calculated from these pieces of information by the following two calculation methods.

(Calculation Method 1) Numerical Information Distance

It is designated which numerical information is to be selected. Assume that numerical information 1 and numerical information 3 are designated. In this case, the similarity degree calculating unit 21 calculates the distance between a vector (numerical information 1, numerical information 3) having numerical information 1 and numerical information 3 in a currently generated report as elements and a vector having, as elements, numerical information 1 and numerical information 3 included in a report including an image candidate, and extracts an image with the distance equal to or less than a designated value as an image with a high similarity degree.

(Calculation Method 2) Attribute Information

It is also possible to select a report exceeding the condition designated by the radiologist. For example, the radiologist can input a condition that the number of links is equal to or more than 1 and the reliability degree of the doctor is equal to or more than 3 as a key for similar image retrieval. If, for example, the condition is satisfied, 1 is returned; otherwise, 0 is returned.

It is possible to calculate a similarity degree by using the above calculation result. For example, calculation is performed in the following order. If the condition of calculation method 2 is not satisfied, the calculation is terminated with 0. If the condition of calculation method 2 is satisfied, a similarity degree is calculated by using the result obtained by calculation method 1. An image with a high similarity degree is extracted. Letting $f(x)$ be a similarity degree, $f(x)=1/x$, $f(x)$ monotonically decreases within the possible range of x, and is a function equal to or more than 0.

The images extracted by the priority calculating unit 22 are output to the interpretation unit 10 in the decreasing order of priorities, and are presented to the radiologist 62 by the terminal 60 via the image output unit 17. Note that when the radiologist 62 evaluates the usefulness of an acquired image and inputs the corresponding value, an operation history updating unit 31 stores the input value in the field "history: operation: evaluation" of the current history in the operation history DB 32. In addition, this embodiment may cause an operation history recording unit 30 to update an operation history, without providing the operation history updating unit 31.

Third Embodiment

FIG. 6 is a block diagram showing the schematic arrangement of the main part of a medical image retrieval system according to the third embodiment. The third embodiment is configured to sequentially retrieve images by discriminating positive and negative instances (to be described in detail later) instead of priorities in the second embodiment. Note that the same reference numerals as in FIG. 6 denote the same parts in FIG. 4, and a detailed description thereof will be omitted.

A positive/negative instance discrimination unit 23 discriminates whether a predicted disease name coincides with a confirmed disease name. More specifically, the positive/negative instance discrimination unit 23 extracts predicted disease names and confirmed disease names in diagnoses corresponding to all examinations by scanning an image DB 25 in advance. The retrieval order is, for example, "examination: report", "report: examination result", "diagnosis: predicted disease name", and "diagnosis: confirmed disease name". The positive/negative instance discrimination unit 23 extracts predicted disease names and confirmed disease names in diagnoses corresponding to all examinations. With regard to image data, a table of examination names and predicted disease names and confirmed disease names for the respective examination regions is generated in a form like that shown in FIG. 7. In this case, an examination name indicates the type of examination such as CT, MRI, or ultrasonic imaging, and an examination region indicates a specific part of the body, e.g., the head or the abdomen. Ideally, a predicted disease name coincides with a confirmed disease name.

For example, it is obvious from the predicted disease name A field in FIG. 7 that there are 91 cases with confirmed disease name A, and three cases with predicted disease name A and confirmed disease name B. The table of FIG. 8 is obtained by dividing the numerical values in each row by the total value at the right end. The table shown in FIG. 8 indicates the ratios of the numbers of cases with confirmed disease names to the total numbers of cases with predicted disease names. For example, the ratio of the number of cases with confirmed disease name A to the number of cases with predicted disease name A is 89.2%; the ratio of the number of cases with confirmed disease name B, 2.9%; the ratio of the number of cases with confirmed disease name C, 1%; and the ratio of the number of cases with "no problem", 6.9%.

The positive/negative instance discrimination unit 23 performs the following processing for each image transferred from a similarity degree calculating unit 21. The following is a specific processing procedure when an input predicted disease name is D.

(1) Extraction of Positive Instances

A pre-designated number of cases are extracted from diagnosis data (pairs of images and reports) with confirmed disease name D in the decreasing order of similarity degrees.

(2) Extraction of Negative Instances

Cases with predicted disease name D and any confirmed disease name other than D are extracted as negative instances. For example, the following two methods are used.

(Method 1)

If the threshold given in advance is 1%, cases mistaken for C (4.0%), cases with "no problem" (2.4%), and cases mistaken for B (1.6%) exceed 1% in the table. A pre-designated number of each case is extracted in the decreasing order of similarity degrees.

(Method 2)

A loss table is prepared in advance (see FIG. 9). Risks are evaluated by using such a loss table and probabilities like those shown in FIG. 8. The result of a loss expected value table is obtained by multiplying mistake probabilities and loss values (see FIG. 10). According to this result, if the loss expected value threshold is 5, cases mistaken for A and cases mistaken for B exceed 5. A pre-designated number of each case is extracted in the decreasing order of similarity degrees.

Fourth Embodiment

This embodiment is associated with an operation history recording unit 30, operation history DB 32, operation template registration unit 40, operation procedure DB 42, and operation history analysis unit 50 in FIG. 1. The constituent elements of this embodiment are the same as those of the first to third embodiments. For this reason, a description of these elements will be omitted, and they will not be illustrated. An operation template will be briefly described first.

Figures 10, 11:
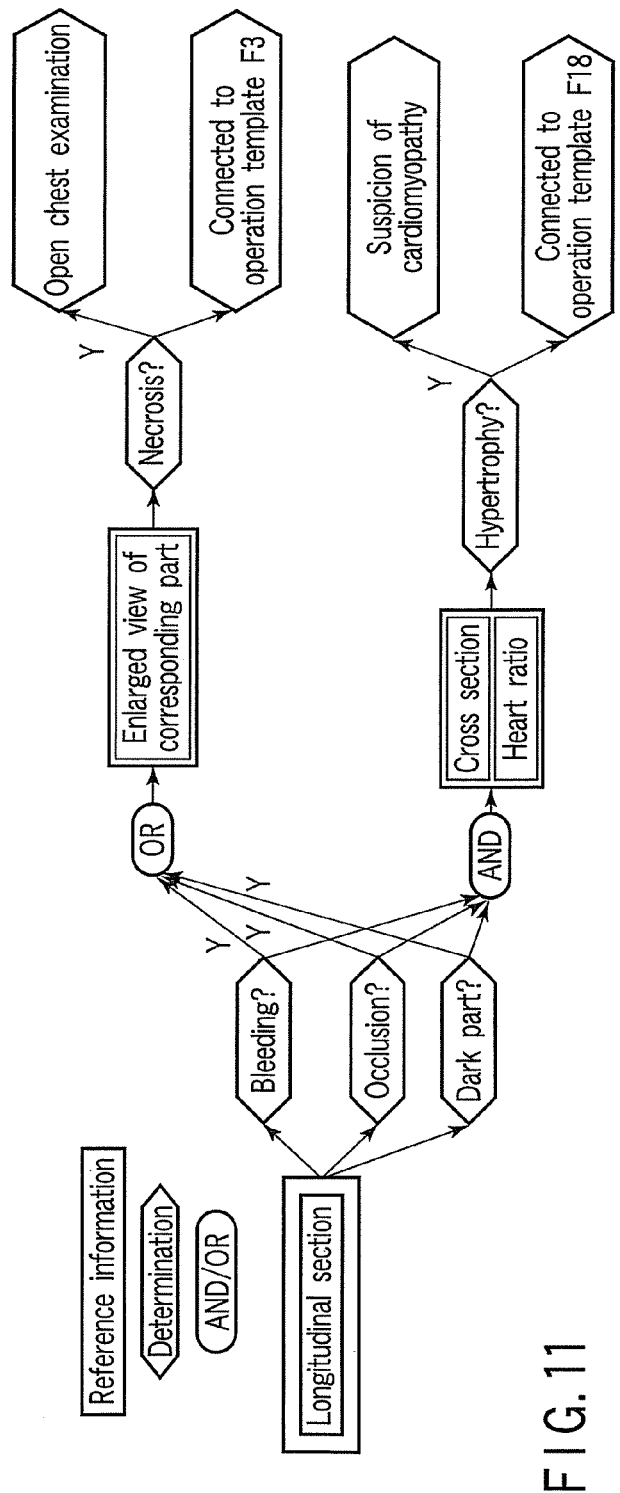
FIG. 10 is a view showing an example of a loss expectation value table.
FIG. 11 is a view showing an example of the data structure of an operation template registered by a radiologist.

An operation template is internally represented as data with a network structure obtained by connecting, via arks, a node indicating information such as an image to be referred in a diagnosis procedure and CAD, nodes indicating branches accompanied with decisions, and nodes indicating logical operation and coupling of decisions under AND/OR conditions. FIG. 11 shows an example of the data structure of an operation template registered by the radiologist. An interpretation unit 10 retrieves this operation template in accordance with the type of diagnosis input to a terminal 60. The operation template shown in FIG. 11 is an example in which a longitudinal section of the heart is referred to first. The radiologist determines "the presence/absence of bleeding", "the presence/absence of vascular occlusion", and "the presence/absence of dark part" from the longitudinal section. If at least one of them is present, the radiologist checks the presence/absence of a necrosis from an enlarged view of the corresponding portion to perform diagnosis to determine whether to perform open chest examination. If there is no necrosis, the process is connected to an operation template F3 (not shown).

If none of "bleeding", "vascular occlusion", and "dark part" is present, the radiologist refers to a cross section of the heart and the heart ratio measured by a CAD system to determine the presence/absence of a hypertrophy. If there is a hypertrophy, the radiologist determines a cardiomyopathy. If there is no hypertrophy, the process is connected to another operation template F18 (not shown). The radiologist registers the prototype of such an operation template in the operation procedure DB 42 by using the operation template registration unit 40.

Figure 12:
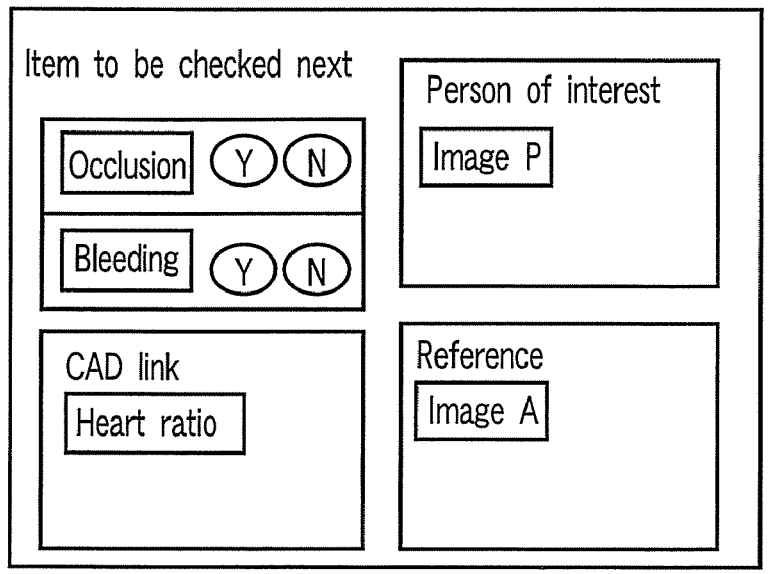
FIG. 12 is a view showing an example of a window at the time of use of an operation template.

An example of a method by which the radiologist uses an operation template will be described next. FIG. 12 is a view showing an example of a window at the time of the use of an operation template. Referring to FIG. 12, the upper left sub-window in the window indicates determination item candidates which are estimated from the operation template in FIG. 11 and should be checked next. Assume that in this case, determination on whether there is a dark part is complete. When the presence/absence of an occlusion and the presence/absence of bleeding are determined, an input window associated with determination on the presence/absence of a necrosis or on the presence/absence of a hypertrophy is displayed on the screen of the terminal 60 by the interpretation unit 10.

The remaining sub-windows in FIG. 12 each indicate information as a reference for diagnosis. The upper right part is a space for displaying an image of the patient himself/herself, the lower right part is a space for displaying an image of a reference case of another patient or typical instance, and the lower left part is a space for displaying CAD measurement values as references. Of these pieces of reference information, a type of information designated by an operation template includes link information for automatic reference. In addition, the radiologist 62 can generate new link information or delete already generated link information by, for example, dragging corresponding information from a retrieval window or dropping corresponding information onto another window at an arbitrary timing, and can record the start and end of display.

Figure 13:
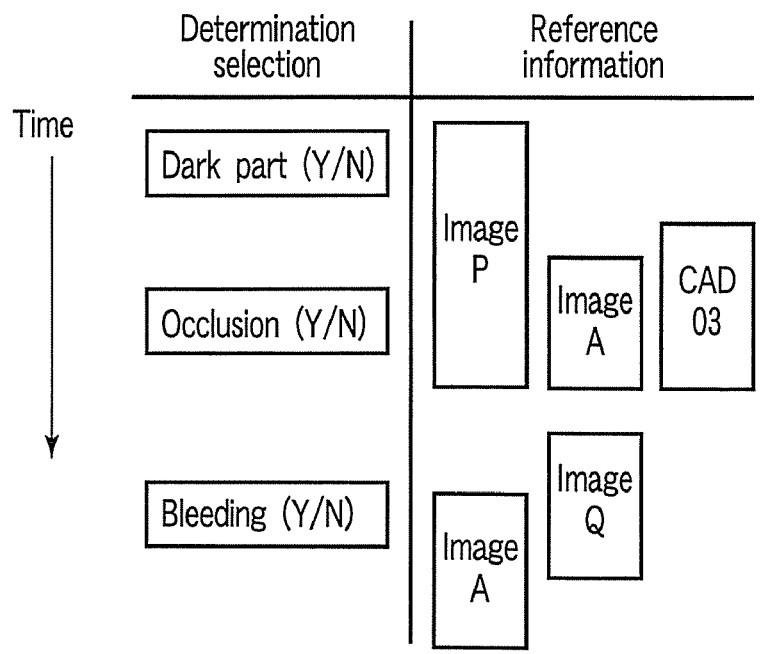
FIG. 13 is a view showing how an operation history at the time of interpretation is recorded.

An operation history at the time of interpretation will be described next. As shown in FIG. 13, when the radiologist 62 diagnoses a retrieved determination case and inputs corresponding information by, for example, pressing a button in the upper left sub-window in the window in FIG. 12 or marking a check at the time of determination, the operation history recording unit 30 records the operation history on the operation history DB 32, together with time data. At the same time, the operation history recording unit 30 records, on the operation history DB 32, the start and end times of reference, together with a determination item execution history, on the basis of each of the ID and link of reference information which has been referred to in the sub-window. If it is possible to check information indicating whether a final diagnosis result is correct, history data corresponding to a correct diagnosis is stored as a positive instance, and history data corresponding to a wrong diagnosis is stored as a negative instance.

When a sufficient amount of operation history data are stored, the operation history analysis unit 50 automatically adds reference information to be retrieved. An image or CAD data with a high frequency of reference at the same time as a given decision step in a given template is identified from the operation history data of a positive instance, and is automatically displayed as retrieval reference information in a sub-window. For example, in determining the presence/absence of an occlusion, if it is determined that the reference frequencies of images P and Q as typical cases are high, the ID of link information of each of the images P and Q is added to the operation template to allow the radiologist to always refer to the images P and Q in a default state, as shown in FIG. 14. Note that in determining a frequency, it suffices to discover reference information satisfying the following condition by using the same idea as that for the discovery of a correlation rule in the data mining field.

Support ((determination i & reference information k)|positive instance)>$\alpha$ Support ((determination i & reference information k)|positive instance)/Support ((reference information k)|positive instance)>$\beta$ where Support ((determination i & reference information k)|positive instance) indicates the frequency with which the reference information k has been displayed upon execution of the determination i in a positive instance. In a strict sense, reference information is not always synchronized with each determination. For this reason, the second mathematical expression is required to estimate the ratio between the frequency with which the reference information k has been displayed upon execution of the determination i and the frequency with which the reference information k has been displayed independently of the determination i.

Assume that no order relationship has been designated in the prototype of an operation template. Even in this case, if an order relationship can be found with a high frequency in the operation history data of a positive instance, a new order relationship is preferably added. In the case of the operation template in FIG. 11, for example, there is no order relationship between the determination on the presence/absence of bleeding, the determination on the presence/absence of an occlusion, and the determination on the presence/absence of a dark part, and hence they can be determined in any order. If, however, the order of "presence/absence of dark part→presence/absence of bleeding" appears with a high frequency in the history data of an actual positive instance, the operation history analysis unit 50 determines that there is some reason for the execution of the determinations in this order, and adds an order relationship as shown in FIG. 15.

Note that in determining a frequency in this case, it suffices to discover reference information satisfying the following condition by using the same idea as that for the discovery of a correlation rule in the data mining field.

Support (determination i ⇒ determination k|positive instance)>$\alpha$

Support (determination i ⇒ determination k|positive instance)/Support (determination k ⇒ determination i|positive instance)>$\beta$ Support (determination i ⇒ determination k|positive instance)/Support (determination i ⇒ determination k)>$\theta$ where Support (determination i ⇒ determination k|positive instance) indicates the frequency with which the determination k has been executed after the determination i in a positive instance, and Support (determination i ⇒ determination k) includes a negative instance. The second mathematical expression indicates that the frequency with which the determination k has been executed after the determination i is sufficiently high compared with the frequency with which the determination i has been executed after the determination k. The third mathematical expression indicates that the frequency with which the determination k has been executed after the determination i in a positive instance is sufficiently higher than the frequency with which the determination k has been executed after the determination i in an overall history including a negative instance.

As described above, according to the embodiments of the present invention, it is possible to automatically retrieve an image as a reference for diagnosis on a target image by using a past diagnosis result and extract and present the retrieved image.

Note that in the above embodiments, the similarity degree calculating unit 21 includes the link counting unit 21a, access counting unit 21b, radiologist reliability degree evaluating unit 21c, and term appearance frequency counting unit 21d. However, the similarity degree calculating unit 21 can include one of them or a combination of two or more components of them.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical image retrieval system comprising:
a processor and memory;
an image database which stores medical images; an interpretation unit which acquires a medical image for use in performing interpretation by a radiologist from the image database and provides the medical image to a computer terminal, wherein each of the medical images is associated with a report including numerical information about diagnosis and attribute information about the report;
a similar example requesting unit which issues an image request requesting a reference image for use with the medical image in performing interpretation;
an image retrieval unit which retrieves the reference image from the image database in accordance with the image request and provides the reference image to the computer terminal in order to propose the reference image as a reference for diagnosis to an user of the computer terminal;
an evaluation input unit which prompts the user of the computer terminal to input an evaluation indicating whether the reference image has been helpful for diagnosis based on the currently diagnosed image,
wherein the image retrieval unit calculates, if a condition provided by the radiologist is satisfied with respect to the attribute information, a similarity degree between a first vector including numerical information of a first report associated with the medical image and a second vector including numerical information of a second report associated with a candidate reference image, and determines the candidate reference image associated with the second report as the reference image in accordance with the calculated similarity degree; and
wherein the attribute information includes at least one of the number of links extending from another report to the candidate reference image associated with the second report, the number of times the candidate reference image associated with the second report has been accessed,
an evaluation value of reliability of a radiologist identified in the second report, and the number of times of appearance of a specific word in the second report.

2. The system according to claim 1, wherein the similar example requesting unit determines whether the reference image is an image of a positive instance in which a predicted disease name coincides with a finally confirmed disease name or an image of a negative instance in which a predicted disease name does not coincide with a finally confirmed disease name.

* * * * *